(12) United States Patent
Peavey

(10) Patent No.: US 7,473,240 B2
(45) Date of Patent: *Jan. 6, 2009

(54) VALVE PORT ASSEMBLY WITH COINCIDENT ENGAGEMENT MEMBER FOR FLUID TRANSFER PROCEDURES

(75) Inventor: Todd Peavey, Watertown, MA (US)

(73) Assignee: Navilyst Medical, Inc., Marlborough, MA (US)

( * ) Notice: Subject to any disclaimer, the term of this patent is extended or adjusted under 35 U.S.C. 154(b) by 755 days.

This patent is subject to a terminal disclaimer.

(21) Appl. No.: 10/634,475

(22) Filed: Aug. 4, 2003

(65) Prior Publication Data

US 2005/0080401 A1 Apr. 14, 2005

Related U.S. Application Data

(63) Continuation of application No. 09/453,999, filed on Dec. 3, 1999, now Pat. No. 6,620,124.

(51) Int. Cl.
*A61M 1/00* (2006.01)
(52) U.S. Cl. ........................... 604/32; 604/248
(58) Field of Classification Search ............. 604/891.1, 604/30, 32, 248
See application file for complete search history.

(56) References Cited

U.S. PATENT DOCUMENTS

| | | | |
|---|---|---|---|
| 2,904,045 A | 9/1959 | Owings | |
| 3,310,048 A | 3/1967 | Ewing | |
| 3,998,222 A | 12/1976 | Shihata | |
| 4,092,983 A | 6/1978 | Slivenko | |
| 4,108,174 A | * 8/1978 | Slivenko | 604/175 |

(Continued)

FOREIGN PATENT DOCUMENTS

WO  WO 97/47338  12/1997

OTHER PUBLICATIONS

*A New Approach in Hemodialysis*, Biolink Corporation, 1999 (4 pages).

(Continued)

*Primary Examiner*—Nicholas D Lucchesi
*Assistant Examiner*—Laura A Bouchelle
(74) *Attorney, Agent, or Firm*—Fay Kaplun & Marcin, LLP

(57) ABSTRACT

An improved valve port system provides blood access in a patient through a subcutaneous fluid flow conduit during a dialysis procedure. The system includes several elements, including a engagement member defined by a tubular body having a proximal end, a distal end and a tubular lumen therebetween. The distal end has a tapered bevel defined thereat and a tapered protrusion proximate thereto defined upon an exterior surface of the tubular body. In addition, the system provides a dialysis port member having a housing with a generally cylindrical valve rotatably positioned therein. The valve includes an open end, a closed end and an orifice near the closed end. The valve further includes a longitudinal groove defined along an interior surface thereof. The groove, which is capable of being in registry with the protrusion, is coincident with the protrusion so as to intussuscept the protrusion therein. In this manner, rotation of the engagement member effects rotation of the valve between an open position wherein the orifice is in fluid communication with the fluid flow conduit and a closed position wherein fluid communication between the orifice and the conduit is precluded.

13 Claims, 3 Drawing Sheets

U.S. PATENT DOCUMENTS

| | | | |
|---|---|---|---|
| 5,169,385 A | | 12/1992 | Turnbull |
| 5,637,088 A | | 6/1997 | Wenner et al. |
| 5,741,228 A | | 4/1998 | Lambrecht et al. |
| 5,931,801 A | | 8/1999 | Burbank et al. |
| 5,989,223 A | * | 11/1999 | Chu et al. .............. 604/167.05 |
| 6,620,124 B1 | * | 9/2003 | Peavey ........................ 604/32 |

OTHER PUBLICATIONS

*An Innovation in Dialysis Access*, © 1999, Vasca, Inc. (3 pages).
*Treating End Stage Renal Disease: The Health and Business Case for Daily Dialysis*, © 1999 Aksys Ltd. (7 pages).

* cited by examiner

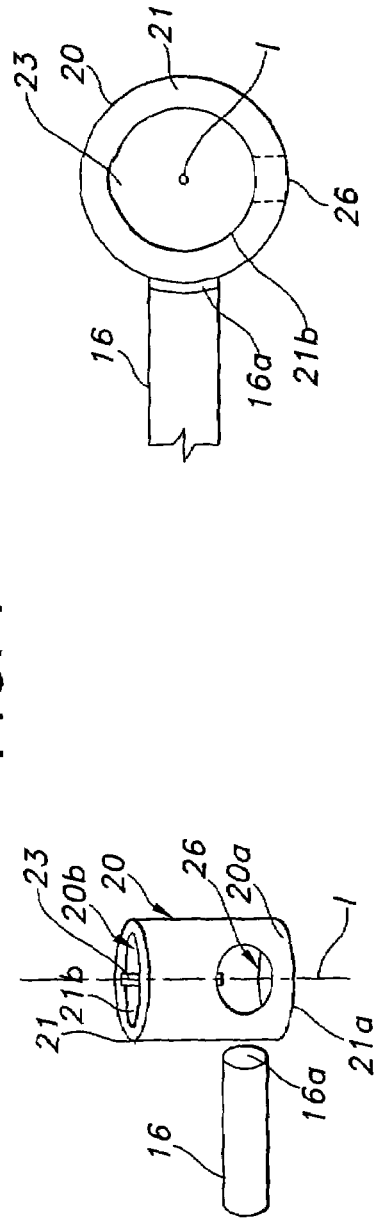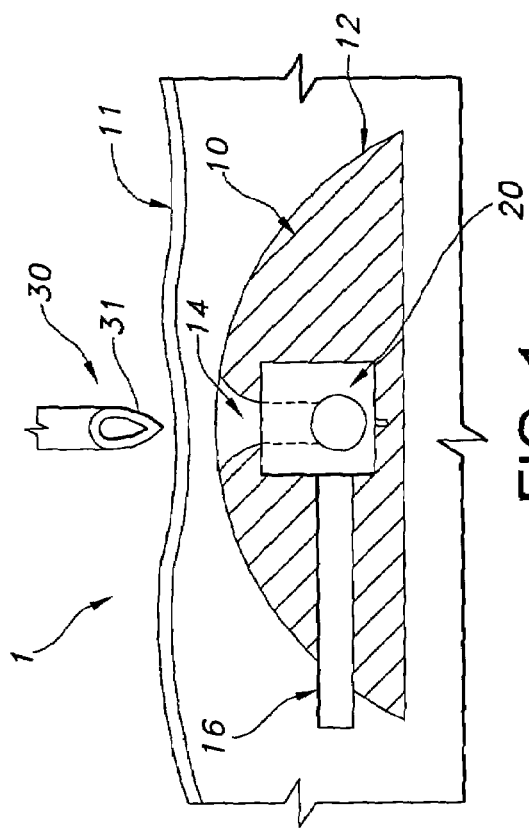

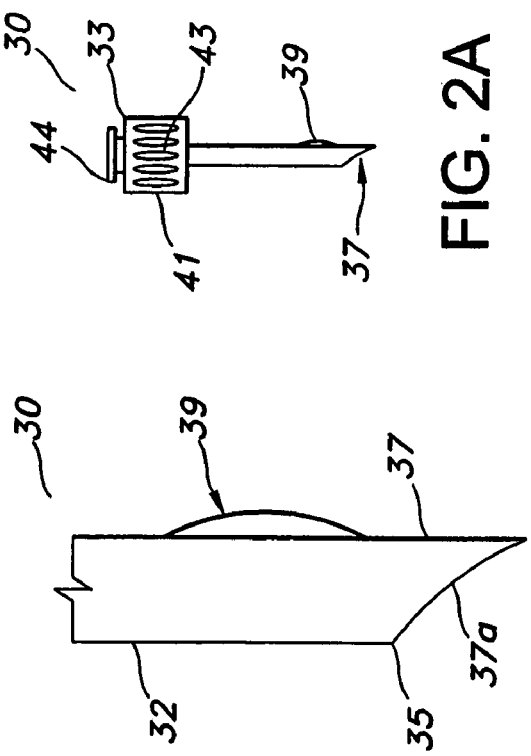
FIG. 2C
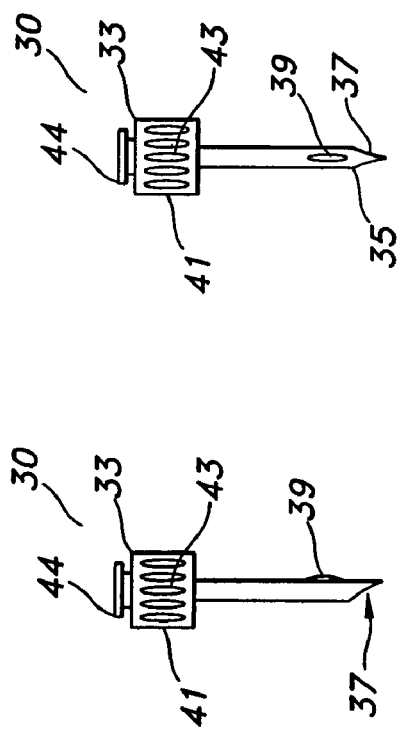
FIG. 2B
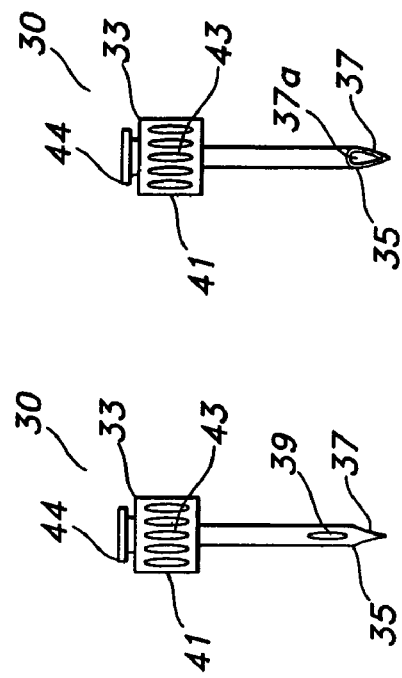
FIG. 2A
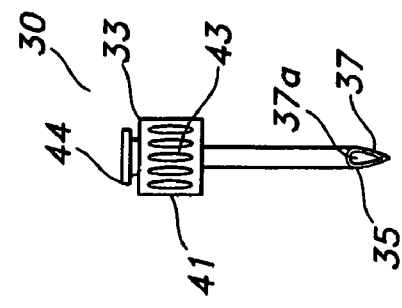
FIG. 2
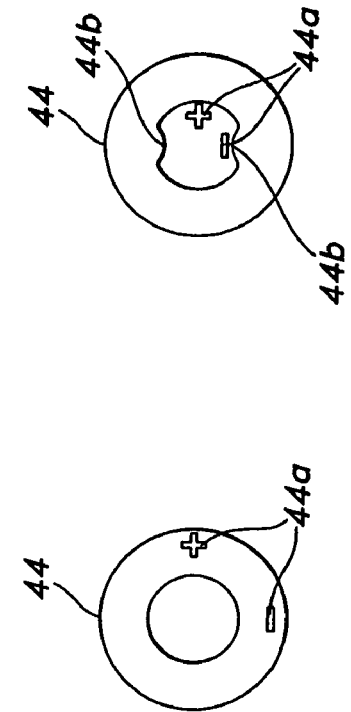
FIG. 2E
FIG. 2D

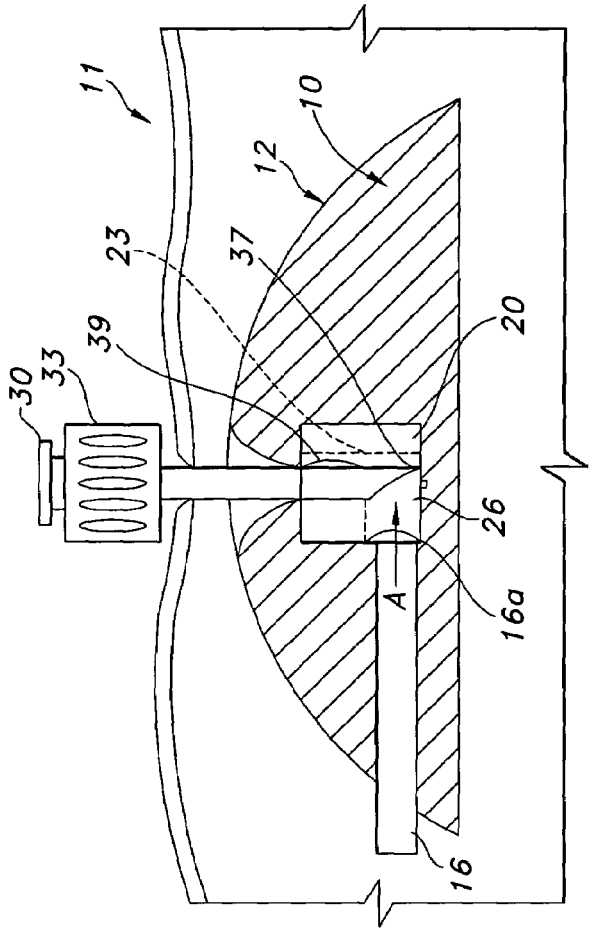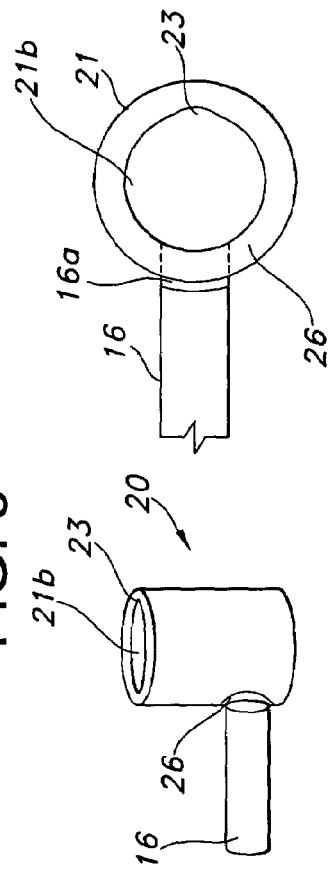

VALVE PORT ASSEMBLY WITH COINCIDENT ENGAGEMENT MEMBER FOR FLUID TRANSFER PROCEDURES

This application is a continuation of application Ser. No. 09/453,999, filed on Dec. 3, 1999 now U.S. Pat. No. 6,620,124.

FIELD OF THE INVENTION

The present invention relates generally to a device that provides percutaneous access to a patient's vascular system during frequently performed fluid transfer procedures such as kidney dialysis. More particularly, the present invention relates to a valve port system having a port member and rotatable valve in combination with an extractable engagement member for insertable accommodation of the member therein.

BACKGROUND OF THE INVENTION

End stage renal disease (ESRD) is a debilitating disorder characterized by the steady decline of kidney function. Healthy kidneys not only clean the blood by filtering out extra water and wastes, but they also produce hormones that maintain strong bones and healthy blood. When the kidneys fail, numerous debilitating effects are experienced, including rising blood pressure, accumulation of fluids and toxic wastes in the body and insufficient red blood cell production. Treatment is therefore required to replace the work of the failed kidneys.

Due to the lack of donor organs and high rate of rejection in kidney transplantation procedures, the majority of ESRD patients rely on one of two dialysis therapies to replace kidney function. The most common treatment is hemodialysis, is a procedure that uses a machine and an artificial kidney to remove toxins and water from a patient's blood. Hemodialysis requires a special filter called a dialyzer to clean the blood. During treatment, blood travels through tubes into the dialyzer, which then filters out waste and extra fluids. The newly cleaned blood flows through another set of tubes and back into the body. Hemodialysis patients typically travel to a dialysis clinic three times per week for 3-4 hours per session.

Peritoneal dialysis is a second procedure that replaces the work of the kidneys. This procedure removes toxins and water through the patient's peritoneal membrane, a large membrane surrounding the organs below the diaphragm. Almost always performed at home, fluids can be exchanged manually four or five times daily or automatically overnight. A cleansing solution, called dialysate, travels through a special tube into the abdomen. Before peritoneal dialysis can be performed, a minor operation is required to insert a soft, plastic tube into the abdomen. A few inches of the tube, or catheter, remains outside the abdomen, but can be hidden by clothing. The catheter is used to connect the patient to bags of dialysate. Fluid, wastes and chemicals pass from tiny blood vessels in the peritoneal membrane into the dialysate. After several hours, the dialysate gets drained from the abdomen, taking the wastes from the blood with it. The abdomen is then filled with clean dialysate and the cleansing process begins again. Peritoneal dialysis is a very time consuming and tedious exchange process, wherein patients experience frequent infections such as peritonitis.

Each of these procedures presents high risks of injury causing loss of vascular access, such as thrombosis, infection, disconnection and hemorrhage. In addition, there are increased risks of fluid volume deficits which may be related to excessive fluid losses, shifts via ultrafiltration, hemorrhage from altered coagulation, disconnection of shunts and fluid restrictions.

Furthermore, studies of patients who require frequent dialysis indicate that numerous treatments of shorter duration can significantly improve clinical outcomes, reduce total treatment costs and improve the quality of life for dialysis patients. It has been proven that the most efficient cleansing of the blood takes place during the first one to two hours of a dialysis session. Increasing the length of time of dialysis is, therefore, not the most efficient way to improve the dose of dialysis. (Source: "Treating End Stage Renal Disease: The Health and Business Case for Daily Dialysis", www.aksys.com, 1999).

Before the initial treatment, access to the bloodstream must be established. The access provides a way for blood to be carried from the body to the dialysis machine and then back into the body. Thus, prior to establishing dialysis treatment, a minor operation is often performed to subcutaneously implant a port in the patient. Ports are totally implantable vascular access devices that permit the infusion of medications, nutrients, blood products and other fluids. Typically, the port includes a chamber and an access region where the chamber is attached to an implanted fluid flow conduit, such as a catheter. The conduit is, in turn, secured to a blood vessel. In the case of veins, the conduit is typically indwelling and in the case of arteries, the conduit may be attached by conventional anastomosis.

Needles and other access tubes may be percutaneously attached to an implanted port in several ways. Conventional blood access designs use an entry needle to force open a gating mechanism leading to a fluid flow conduit in fluid communication with a subcutaneous port. These designs are not always airtight and often require additional mechanisms so that a heparin lock may be established between treatment sessions. Furthermore, any entry or activation needle must be secured within the port body throughout the procedure, providing an opportunity for the needle to withdraw during the dialysis procedure. Numerous attempts have been made to provide dialysis access devices which overcome the above described problems. Examples of such devices are described in U.S. Pat. No. 3,998,222 to Shihata which discloses a subcutaneous shunt having an axially and rotatably movable valve therein; and U.S. Pat. No. 4,092,983 to Slivenko which discloses a blood access device wherein a pair of tubular conduits is provided on a generally cylindrical housing. Other systems that are currently marketed as solutions to the vascular access dilemma include a dual-access port and catheter access system known as Dialock (a registered trademark of Biolink of Middleboro, Mass.) and an implantable valve and cannula system known as LifeSite (a trademark of Vasca, Inc. of Tewksbury, Mass.).

The number of ESRD patients worldwide requiring dialysis is growing at a significant rate. This growth is primarily attributable to an aging population and the increasing life expectancy of patients with a high risk of ESRD. Yet, even in view of the increasing need for more frequent vascular access and the growing numbers of patients requiring such treatment, none of the above described devices provides the critical combination of (1) a needle that establishes and maintains heightened efficiency of blood flow so as to reduce the discomfort experienced by the patient and (2) a subcutaneous device actuatable by the needle that not only assists the needle with such efficiency, but also prevents inadvertent needle withdrawal. Furthermore, such devices do not address the need to control needle bevel orientation, which is critical to maximizing blood flow rates and the overall efficiency of the dialysis procedure. If the bevel opening faces a wall or is obstructed in any way, flow will be adversely affected, thereby lengthening and complicating the dialysis procedure.

It is therefore desirable to provide a system which obviates the above mentioned problems while reducing the number of components required to effect successful dialysis and other fluid transfer procedures. Such a system would provide an implantable port which only permits fluid flow upon establishment of fluid communication between an engagement member and a fluid flow conduit, such fluid communication being selectively established by mating of the engagement member with the dialysis port.

SUMMARY OF THE INVENTION

It is an advantage of the present invention to provide a dialysis assembly which accommodates frequent access to a subcutaneously implanted dialysis port.

It is another advantage of the present invention to provide a dialysis port assembly that precludes withdrawal of an activation needle during a dialysis procedure.

It is yet another advantage of the present invention to provide a dialysis port assembly having a rotatable valve therein, such that the rotatable valve has an orifice that is alignable with a fluid flow conduit to control the flow of blood via the port member.

It is still another advantage of the present invention to provide an activation needle having a low profile protrusion thereon for corresponding engagement with a groove defined longitudinally along an interior surface of the rotatable valve, such that rotation of the needle effects rotation of the valve between an open position, wherein an orifice in the valve is in fluid communication with a fluid flow conduit, and a closed position, wherein fluid communication between the orifice and the conduit is precluded.

The present invention provides these and other advantages by furnishing a valve port system for percutaneous vascular access to a patient during dialysis and other fluid transfer procedures. The system includes a tubular engagement member and a valve rotatably positioned within a subcutaneously implantable port member housing. In the present invention, vascular access is effected through a subcutaneously implantable fluid flow conduit in communication with the port housing. The port establishes fluid flow communication between the conduit and the engagement member for the transport of blood, medicaments and other fluids therebetween.

The engagement member of the present invention is designed to prevent extraction of the engagement member from the port during a fluid transfer procedure. The engagement member is defined by a tubular body having a proximal end, a distal end and a tubular lumen therebetween. The distal end has a tapered bevel defining an opening thereat. A tapered protrusion proximate the distal end is defined upon an exterior surface of said tubular body.

The engagement member of the present invention is also designed to be engageable with the rotatable valve. The valve is a generally cylindrical body having an open end, a closed end and an orifice proximate said closed end. The body is rotatable about its central axis between an open position, when the orifice is in fluid communication with the conduit, and a closed position, wherein such fluid communication is precluded. The valve includes a longitudinal groove defined along its interior surface which is capable of being in registry with the protrusion of the engagement member. The groove is coincident with the protrusion for intussusception of the protrusion therein. In this configuration, rotation of the engagement member effects rotation of the valve between an open position, when the orifice is in fluid communication with the conduit, and a closed position, when fluid communication between the orifice and the conduit is precluded.

BRIEF DESCRIPTION OF THE DRAWINGS

FIG. 1 shows a perspective view of a valve port assembly of the present invention prior to use in a fluid transfer procedure.

FIG. 1A shows a perspective view of a rotatable valve of the valve port system of FIG. 1 in a closed configuration in relation to a subcutaneously implanted fluid flow conduit positioned thereadjacent.

FIG. 1B shows a top view of a rotatable valve of FIG. 1A having a longitudinal groove and an orifice defined therein.

FIG. 2 shows a partial side view of an engagement member of the system of FIG. 1, the engagement member having a low profile protrusion defined thereon.

FIGS. 2A, 2B and 2C show side, front and back views, respectively, of the engagement member of FIG. 2.

FIGS. 2D and 2E show top views of alternating embodiments of a pull knob defined on the engagement member of FIG. 2.

FIG. 3 shows the valve port system of the present invention during use in a fluid transfer procedure.

FIG. 3A shows a perspective view of a rotatable valve of the system of FIG. 3 in an open configuration in relation to a subcutaneously implanted fluid flow conduit positioned thereadjacent.

FIG. 3B shows a top view of the rotatable valve of FIG. 3A showing a valve orifice in alignment with a conduit opening.

DETAILED DESCRIPTION OF THE PREFERRED EMBODIMENTS

The valve port system of the present invention provides a port member having a housing with a valve rotatably positioned therein. The port housing insertably accommodates a fluid flow conduit such as a catheter tube therein so that the conduit is capable of providing fluid flow communication between the patient's vascular system and a dialyzer, catheter or other blood transport device. The valve is a generally cylindrical member having an open end, a closed end and an orifice positioned near the closed end which is rotatably alignable with the conduit. In addition, a longitudinal groove is defined along an interior surface of the valve. An extractable engagement member such as needle is also provided, having an elongate tubular body defined by a proximate end and a distal end. A tapering bevel defines an opening at the distal end so as to form a tip thereat. A low profile protrusion is defined proximate the distal end at a position that enables engagement of the protrusion in the longitudinal groove. The engagement member is insertable in the valve and engageable therewith when the protrusion is in registry with the groove. The groove accommodates the protrusion therein as the engagement member is inserted distally in the valve. In this position, the engagement member, and thus the valve, is rotatable between an open position, wherein the orifice is in fluid communication with the conduit, and a closed position wherein such fluid communication is precluded. The position of the protrusion ensures that the bevel opening coincides with the orifice when the valve is in the open position to facilitate efficient blood flow between the conduit and the needle.

The engagement member and valve of the present invention are designed so that while the conduit is open, the engagement member is secured into a position which allows fluid exchange yet prohibits needle extraction during a fluid transfer procedure. This design minimizes the number of required moving parts, thereby optimizing the durability of the system. As a consequence, the present design eliminates the possibility of inadvertent valve opening and simplifies the design and manufacture of the system.

Now referring to the drawings wherein like elements are identically numbered, a valve port system 1 of the present invention is provided in FIG. 1. The primary components of system 1 include a port member 10 subcutaneously implanted under skin tissue 11 and having a housing 12 thereabout with a port opening 14 provided therein; a generally cylindrical valve 20 rotatably housed within port member 10; and an extractable engagement member 30 having a tapered bevel 31, the engagement member shown in alignment for insertion in port opening 14. Port housing 12 also insertably accommodates a fluid flow conduit 16 therein, wherein conduit 16 is a fluid transport device such as a catheter. Port member 10, via conduit 16 and port opening 14, establishes fluid communication between the patient's vascular system and engagement member 30 when the engagement member punctures skin tissue 11 and infiltrates port housing 12.

Referring further to FIGS. 1A and 1B, valve 20 is a rotatable member having an exterior surface 20a and an interior surface 20b defining a generally cylindrical wall 21 therebetween. Wall 21 is closed at one end 21a and opens up at an opposite end 21b to reveal a longitudinal groove 23 along interior surface 20b. Groove 23 is defined so as to be parallel with valve 20's central longitudinal axis l.

As further illustrated in the figures, valve 20 also includes an orifice 26 defined near closed end 21a. Orifice 26 conforms to an opening 16a in conduit 16, which conduit lies adjacent valve 20 so as to ensure relatively frictionless rotation of valve 20 relative to conduit 16. Opening 16 is adapted to conform to cylindrical wall 21 so as to form a fluid proof seal therebetween.

Now referring to FIGS. 2-2E, a engagement member used in conjunction with the present system is provided. Engagement member 30 has a generally tubular body 32 having a proximal end 33 which remains above skin tissue 11, a distal end which protrudes beneath skin tissue 11 and into port opening 14, and a tapered bevel 37 defined at distal end 35. Bevel 37 delineates an opening 37a thereat, which opening conforms to the parameters of orifice 26 in valve 20.

Proximate bevel 37 is a low profile protrusion 39 defined on an exterior surface of tubular body 32. Protrusion 39 is positioned on body 32 so as to permit easy insertion and removal of engagement member 30 into valve 20 and permit rotation of valve 20 thereby. Although protrusion 39 is shown as having a generally parabolic profile, any low profile configuration can be implemented which is conducive to the operation of the present system and which fulfills the objectives enumerated herein.

Engagement member 30 preferably includes a gripping member 41 at proximal end 33. Gripping member 41 may have a plurality of tactile indicia 43 (i.e. elongate recesses) defined thereabout to facilitate gripping and torquing of the engagement member by the user. Gripping member 41 may further include an elevated pull knob 44 defined thereon to enable easy insertion and extraction of engagement member 30 from a patient. Pull knob 44 may include visual indicia 44 to indicate when engagement member 30 has been sufficiently rotated to permit fluid transfer therethrough. Pull knob 44 may also include tactile indicia 44b to fit a user's thumb and forefinger when inserting or extracting engagement member 30 from the patient.

Having described the components, the operation and function of the present invention connector can now be described, with particular reference to FIGS. 3-3B.

In a method of employing the present invention in a fluid transfer procedure such as that which occurs in dialysis, port member 10 is subcutaneously implanted along with conduit 16 so that port housing 12 provides a housing for conduit 16. To initiate a fluid flow transfer procedure, engagement member 30, and more particularly, bevel 37, is aligned with port opening 14 and inserted through skin tissue 11 into port opening 14. Such alignment is effected by establishment of a fistula in the patient, which process is well known in the art.

After percutaneous insertion through skin tissue 11, engagement member 30 is guided toward port opening 14 so that protrusion 39 is in registry with groove 23. In this initial configuration, valve 20 is in the closed position as shown in FIGS. 1-1B. It is noted that during insertion of engagement member 30, bevel opening 37a is always aligned with orifice 26. The location of protrusion 39 on distal end 35 of engagement member 30, therefore, must accommodate engagement member 30 so as to always maintain this alignment during the fluid transfer procedure.

In order to initiate fluid flow between conduit 16 and engagement member 30, it is necessary to rotate valve 20 from an initial closed position, wherein orifice 26 is not in fluid communication with conduit opening 16a (as shown in FIGS. 1 and 1A), to a subsequent open position wherein orifice 26 and conduit opening 16a are in fluid communication (as shown in FIGS. 3 and 3A). To effect such rotation, engagement member 30 is inserted into valve 20 so that groove 23 engages protrusion 39 therein. Groove 23, which is capable of being in registry with protrusion 39, is rotatably aligned with protrusion 39. Groove 23 is coincident with protrusion 39, therefore permitting intussusception of engagement member 30 in valve 20.

To place valve 20 in the open position, engagement member 30 is advanced percutaneously into port opening 14 until it is fully mated with valve 20. A user then grasps gripping member 41 to rotate engagement member 30 a sufficient angular distance to open the flow conduit 16 for infusion of blood in the direction indicated by arrow A. Although a 90° rotation is illustrated in the drawings, any angular rotation may be effected that requires in comportment with the operation and objectives of the present invention.

Because engagement member 30 is now locked in valve 20, rotation of engagement member 30 effects corresponding rotation of valve 20 from the closed position to the open position (shown in FIG. 3). In the open position, orifice 26 is in alignment with conduit opening 16a, allowing fluid to flow from conduit 16 into engagement member 30. Once rotated into the open position, engagement member 30 is secured within port housing 12 and cannot be withdrawn. Thus, orifice 26 and bevel opening 37a are always maintained in alignment with conduit opening 16a to maximize the efficiency of fluid flow.

At the conclusion of a treatment session, engagement member 30 is rotated in a direction opposite that in which the open position was achieved, thereby sealing conduit opening 16a and preventing further fluid communication therebetween. It is then possible to extract engagement member 30 from port housing 12.

The rotating valve design as shown herein is advantageous, for such a design provides an airtight conduit seal that establishes a heparin lock between treatment sessions and eliminates additional mechanisms, such as gates and the like, that are provided in conventional vascular access devices. The rotating valve also ensures optimal needle orientation for maximizing flow rates, such that the needle and valve design together ensure that the bevel is correctly oriented to achieve maximum blood flow. The complementary configuration of the rotating valve also ensures full closure of the conduit prior to needle removal and further ensures needle securement within the port during a fluid transfer (i.e. dialysis) procedure.

In the present invention, a subcutaneous port and activation needle are designed to provide central venous access for the purpose of frequently performed fluid transfer procedures such as dialysis. Due to the frequency of such procedures and the consequential negative effects on a patient's comfort and physical and psychological health, it is necessary to prevent premature extraction of needles and further ensure efficient transfer of blood via a subcutaneously implanted port member. The present invention, therefore, provides not only an improved port member and valve assembly, but also provides an improved engagement member compatible therewith. The engagement member optimizes bevel orientation for maximum flow rates and ensures full closure of a fluid flow conduit. By designing this present system with such safeguards, patients requiring frequent dialysis and other fluid transfer treatments are spared painful and lengthy vascular access procedures.

Various changes to the foregoing described and shown methods and corresponding structures would now be evident to those skilled in the art. Accordingly, the particularly disclosed scope of the invention is set forth in the following claims.

What is claimed is:

1. A kit of parts adapted to establishing percutaneous vascular access to a patient during a fluid transfer procedure, said kit comprising:

a valve port system for providing vascular access in a patient through a subcutaneous fluid flow conduit during a dialysis procedure;

an extractable engagement member for percutaneous patient entry defined by a tubular body having a proximal end, a distal end and a tubular lumen therebetween, said distal end having a tapered bevel defining an opening threat and a tapered protrusion proximate thereto defined upon an exterior surface of said tubular body, said protrusion having a generally parabolic profile; and a port member having a housing with a generally cylindrical valve rotatably positioned therein, said rotatable valve having an open end, a closed end and an orifice proximate said closed end, said body being rotatable about its central axis between an open position and a closed position; said valve further having a longitudinal groove defined along an interior surface thereof capable of being in registry with said engagement member protrusion, said groove coincident with said protrusion for intussusception of said protrusion therein such that rotation of said engagement member effects rotation of said valve between said open and closed positions.

2. The kit of parts of claim 1 wherein said conduit lies adjacent said valve so as to ensure relatively frictionless rotation said valve relative to said conduit.

3. The kit of parts of claim 2 wherein said conduit has an opening proximate said closed end of said valve.

4. The kit of parts of claim 3 wherein said orifice is in fluid communication with said conduit opening in said open position.

5. The kit of parts of claim 3 wherein fluid communication between said conduit opening and said orifice is precluded in said closed position.

6. The kit of parts of claim 1 wherein said bevel opening is in alignment with said orifice.

7. The kit of parts of claim 6 wherein protrusion is located proximate said bevel opening.

8. The kit of parts of claim 7 wherein said protrusion is located in semi-circumferential relationship relative to said bevel opening.

9. The kit of parts of claim 1 wherein said bevel opening conforms to said orifice.

10. The kit of parts of claim 1 wherein said engagement member further includes a gripping member at said proximal end.

11. The kit of parts of claim 10 wherein said gripping member has a plurality of tactile indicia defined thereabout to facilitate gripping and torquing of said engagement member.

12. The kit of parts of claim 10 wherein said gripping member further includes a turn knob defined thereon.

13. The kit of parts of claim 12 wherein said turn knob includes indicia to indicate rotation of said valve between said open and closed positions.

* * * * *